(12) United States Patent
Yamano

(10) Patent No.: US 8,495,915 B2
(45) Date of Patent: Jul. 30, 2013

(54) ULTRASONIC TESTING METHOD AND MANUFACTURING METHOD OF SEAMLESS PIPE OR TUBE

(75) Inventor: Masaki Yamano, Suita (JP)

(73) Assignee: Nippon Steel & Sumitomo Metal Corporation, Tokyo (JP)

( * ) Notice: Subject to any disclaimer, the term of this patent is extended or adjusted under 35 U.S.C. 154(b) by 761 days.

(21) Appl. No.: 11/990,934

(22) PCT Filed: Aug. 28, 2006

(86) PCT No.: PCT/JP2006/316871
§ 371 (c)(1),
(2), (4) Date: Sep. 30, 2009

(87) PCT Pub. No.: WO2007/024001
PCT Pub. Date: Mar. 1, 2007

(65) Prior Publication Data
US 2010/0005846 A1   Jan. 14, 2010

(30) Foreign Application Priority Data

Aug. 26, 2005  (JP) .................................. 2005-245475
Jun. 26, 2006  (JP) .................................. 2006-175610

(51) Int. Cl.
*G01N 29/24*  (2006.01)
*G01N 29/26*  (2006.01)

(52) U.S. Cl.
USPC ............................................. 73/602; 73/622

(58) Field of Classification Search
USPC ................................................... 73/602, 622
See application file for complete search history.

(56) References Cited

U.S. PATENT DOCUMENTS

| 4,164,150 A | * | 8/1979 | Ries et al. ........................ 73/644 |
| 4,289,033 A | * | 9/1981 | Prause et al. .................... 73/622 |
| 4,679,437 A | * | 7/1987 | Koike et al. ..................... 73/622 |
| 4,740,146 A | * | 4/1988 | Angelbeck ....................... 425/71 |

FOREIGN PATENT DOCUMENTS

| EP | 981047 A2 | * | 2/2000 |
| JP | 58-171663 |   | 10/1983 |
| JP | 61-18860  |   | 1/1986 |
| JP | 61-93952  |   | 5/1986 |
| JP | 2-67957   |   | 3/1990 |
| JP | 4-142456  |   | 5/1992 |
| JP | 9-72887   |   | 3/1997 |
| JP | 10090239 A | * | 4/1998 |
| JP | 11-108902 |   | 4/1999 |
| JP | 2005-211973 |  | 8/2005 |
| JP | 2005-221371 |  | 8/2005 |
| JP | 2006177845 A | * | 7/2006 |

* cited by examiner

*Primary Examiner* — Peter Macchiarolo
*Assistant Examiner* — Rose M Miller
(74) *Attorney, Agent, or Firm* — Clark & Brody

(57) ABSTRACT

A circumferential angle of incidence αi of an ultrasonic wave transmitted from an ultrasonic probe 1 upon a tubular test object P and an axial angle of incidence βi of the ultrasonic wave transmitted from the ultrasonic probe 1 upon the tubular test object P are set based on a ratio of thickness to outer diameter t/D of the tubular test object P so that an internal refraction angle θk calculated from the circumferential angle of incidence αi, the axial angle of incidence βi, and the ratio of thickness to outer diameter t/D of the tubular test object may be not less than 35° and not more than 60°.

9 Claims, 7 Drawing Sheets

ULTRASONIC TESTING METHOD AND MANUFACTURING METHOD OF SEAMLESS PIPE OR TUBE

TECHNICAL FIELD

The present invention relates to a ultrasonic testing method for detecting, by using ultrasonic waves, an internal surface flaw of a tubular test object such as a steel pipe or tube and a method for manufacturing a seamless pipe or tube by using this ultrasonic testing method and, more specifically, to an ultrasonic testing method capable of detecting internal surface flaws having various tilt angles with respect to an axial direction of a tubular test object with almost the same detectability irrespective of a ratio of thickness to outer diameter and tilt angles of the internal surface flaws of the tubular test object, and a seamless pipe or tube manufacturing method using this ultrasonic testing method.

BACKGROUND ART

As demand for higher quality pipes or tubes grows in recent years, there is an increasing trend that nondestructive test standards for the pipes or tubes (hereinafter referred to as "pipes" when deemed appropriate) are becoming more stringent.

For example, a seamless pipe, which is a typical pipe, is manufactured by punching a billet with a piercer to form a hollow shell and rolling the hollow shell with a mandrel mill or the like. The seamless pipe has flaws having various tilt angles (hereinafter referred to as "tilted flaws" when deemed appropriate) with respect to the axial direction.

A tilted flaw is believed to be caused by deformation in the axial direction of a longitudinal crack originally existing on the billet in the above manufacturing process or transfer of a flaw existing on a guide face of a guide shoe for maintaining a path center of a hollow shell. Therefore, the tilt angle of the tilted flaw with respect to the axial direction of the seamless pipe changes depending on a difference in a pipe diameter of the seamless pipe or a cause for occurrence thereof. That is, there are tilted flaws with various tilt angles on the seamless pipe.

Since there is a trend of tighter service conditions of the seamless pipes from year to year, higher quality is demanded and accurate detection of the above tilted flaws is also sternly demanded.

Conventionally, various methods for detecting the tilted flaws existing on the seamless pipes have been proposed.

In Japanese Laid-Open Patent Publication No. 55-116251 (hereinafter referred to as "Patent Literature 1"), for example, a method for detecting a tilted flaw by arranging an ultrasonic probe at an appropriate position and tilt angle depending on the position and tilt angle of the tilted flaw to be detected is proposed.

However, the method described in Patent Literature 1 has a problem that extremely much time and manpower are needed because the tilt angle of the ultrasonic probe must be changed each time in accordance with the tilt angle of the tilted flaw to be detected. Also, to detect tilted flaws with various tilt angles existing on the seamless pipe in one round of flaw-detecting work, as described above, many ultrasonic probes must be provided, each of which is arranged with a different tilt angle. That is, there are problems that large equipment is required and soaring costs are entailed, in addition to complicated arrangements/settings and calibration of ultrasonic probes.

To solve the problems of the method described in the above Patent Literature 1, a flaw detecting method that applies an ultrasonic phased array probe in which a plurality of transducers (elements for transmitting/receiving ultrasonic waves) are arranged in a single row is proposed in Japanese Laid-Open Patent Publication No. 61-223553 (hereinafter referred to as "Patent Literature 2"). More specifically, ultrasonic shear waves are propagated within the pipe by aligning an arrangement direction of the transducers with the axial direction of the pipe and arranging the ultrasonic probe decentralized from an axial center of the pipe. Then, according to this method, the tilted flaws with the various tilt angles are detected by changing the tilt angle (tilt angle with respect to the axial direction of the pipe) of ultrasonic waves transmitted and received by the ultrasonic probe using electronic scanning that electrically controls transmission/reception time-shift of the ultrasonic wave by each transducer.

However, the method of Patent Literature 2 has the following problems mainly.

FIG. 1 shows a diagram illustrating an example of a relation between the tilt angle (angle formed by an extension direction of the tilted flaw and the axial direction of the pipe) of the tilted flaws and echo intensity according to an ultrasonic testing method applying an ultrasonic phased array probe, verified by an experiment conducted by the inventor of the present invention. More concretely, FIG. 1 shows echo intensity (relative intensity when the echo intensity of a tilted flaw with the tilt angle 0° is defined to be 0 dB) of each tilted flaw when, in a state where an ultrasonic phased array probe equivalent to that described in Patent Literature 2 is arranged with a constant eccentricity from the axial center of the pipe, the tilt angle of the ultrasonic wave is changed by electronic scanning in accordance with the tilt angle of each tilted flaw so that the extension direction of the tilted flaw and a propagation direction (propagation direction viewed from a normal direction of a tangential plane of the pipe including an incident point of the ultrasonic wave) of the ultrasonic wave transmitted by the ultrasonic probe are orthogonal to each other. The inventor of the present invention has found a problem that, as shown in FIG. 1, echo intensity is different depending on the tilt angle of the tilted flaw even if the tilted flaw is of the same size (0.5 mm in depth and 25 mm in length).

The inventor of the present invention has found that this problem is caused by a fact that if tilt angles of ultrasonic waves are changed through electronic scanning according to the tilt angles of the respective tilted flaws in condition where an eccentricity of the ultrasonic phased array probe is set to a constant value so that an extending direction of the tilted flaws may be orthogonal to a propagation direction of the ultrasonic waves transmitted by the ultrasonic probes, an angle (internal refraction angle) formed by a normal of the pipe at a point where the ultrasonic wave (center line of an ultrasonic wave beam) that has entered the pipe reaches an internal surface of the pipe and the ultrasonic wave (center line of the ultrasonic wave beam) and an angle (external refraction angle) formed by a normal of the pipe at a point where the ultrasonic wave (center line of the ultrasonic wave beam) that has entered the pipe reaches an external surface of the pipe and the ultrasonic wave (center line of the ultrasonic wave beam) vary with:

(1) eccentricities of the ultrasonic probes;

(2) tilt angles of the ultrasonic waves owing to electronic scanning; and (3) a ratio of thickness (t) to outer diameter (D) of the pipes (=t/D).

As described above, the inventor of the present invention has found that the method described in Patent Literature 2 has the problem that the echo intensity is different depending on the tilt angle of the tilted flaw and there is a possibility that this problem may prevent detection of a harmful flaw or lead to over-detection of minute flaws that need not be detected.

On the other hand, Japanese Laid-Open Patent Publication No. 2005-221371 (hereinafter referred to as "Patent Literature 3") proposes an ultrasonic testing method for using an ultrasonic phased array probe in which each of transducers has a pipe-axial tilt (which corresponds to the above-described ultrasonic wave tilt angle) of an transducer derived from a tilt of a flaw (which corresponds to the above-described tilt angle of the tilted flaw) and a flaw detection angle of refraction (=above-described external refraction angle) and a pipe-circumferential angle of incidence (which corresponds to a pipe-circumferential angle of incidence determined based on the above-described eccentricities).

According to the method disclosed in Patent Literature 3, based on a pipe-axial tilt and a pipe-circumferential angle of incidence of each of the transducers, a tilted flaw having a specific tilt angle (especially, an external surface flaw present on the external surface of the pipe) can be detected highly accurately. However, this method has a problem that detectability deteriorates for a tilted flaw having a tilt angle different from that at a time of designing the ultrasonic probes.

Further, according to the method disclosed by Patent Literature 3, detectability tends to deteriorate more for an internal surface flaw than for an external surface flaw, so that the internal surface flaw may be missed. The inventor of the present invention has found that this problem is caused by a fact that an internal refraction angle becomes too larger as compared to an external refraction angle owing to a ratio of thickness to outer diameter of the pipe and a tilt angle of the tilted flaw.

Moreover, Japanese Laid-Open Patent Publication No. 5-249091 (hereinafter referred to as "Patent Literature 4") proposes an ultrasonic testing method for detecting a tilted flaw having a desired tilt angle in condition where an angle of incidence of an ultrasonic wave upon a pipe is kept constant (that is, an external refraction angle is kept constant) by rotating an ultrasonic probe along a side face of a cone that has a point of incidence of the ultrasonic wave upon the pipe as its vertex and a normal at this point of incidence as its central axis.

However, the method disclosed in Patent Literature 4 also has a problem that detectability deteriorates more for an internal surface flaw than for an external surface flaw because an internal refraction angle becomes too larger as compared to an external refraction angle, which is a constant value, depending on a ratio of thickness to outer diameter of a pipe and a tilt angle of a tilted flaw.

In other words, the methods disclosed in Patent Literatures 3 and 4 both have a problem of difficult detection owing to deteriorated detectability of an internal surface flaw depending on a ratio of thickness to outer diameter of a pipe and a tilt angle of a tilted flaw, because setting of flaw detection condition is based on an external refraction angle that can be derived from a propagation speed of an ultrasonic wave (ultrasonic longitudinal wave) through a coupling medium that fills a gap between an ultrasonic probe and the pipe, a propagation speed of the ultrasonic wave (ultrasonic shear wave) through the pipe, and an angle of incidence of the ultrasonic wave upon the pipe in accordance with the Snell's law.

DISCLOSURE OF THE INVENTION

As described above, the conventional ultrasonic testing method has a problem that detectability deteriorates for an internal surface flaw present on an internal surface of a pipe depending on a ratio of thickness to outer diameter of the pipe and a tilt angle of the tilted flaw, in which detection of internal surface flaws by means of ultrasonic testing method may well be important more than detection of external surface flaws. This is because detection of external surface flaws including visual inspection can be easily carried out also by any other NDI methods such as eddy current testing method and magnetic leakage flux testing method. In contrast, detection of internal surface flaws by means of visual inspection, eddy current testing method, or magnetic leakage flux testing method is liable to have a necessity of inserting an appropriate sensor head into the pipe, which leads to a problem that inspection time tends to be prolonged and a sensor head inserting mechanism tends to be larger in size and complicated.

It is to be noted that problems of the above-described conventional technologies are not limited to a case where a test object is a seamless pipe, but are common to ultrasonic testing of all types of tubular test objects in which tilted flaws may occur including a welded pipe such as a spiral pipe, and a hollow axle.

To solve these problems of the conventional technologies, the present invention has been developed, and it is an object of the present invention to provide an ultrasonic testing method capable of detecting internal surface flaws having various tilt angles with respect to an axial direction of a tubular test object with almost the same detectability irrespective of a ratio of thickness to outer diameter and tilt angles of the internal surface flaws of the tubular test object, and a seamless pipe manufacturing method using this flaw detection method.

The inventor of the present invention discussed devotedly to solve the above-described problems and, as a result, found that only by setting flaw detection condition so that an internal refraction angle may be not less than 35° and not more than 60°, it is possible to substantially equalize intensities of echoes reflected by internal surface flaws and, accordingly, detect the internal surface flaws with almost the same detectability irrespective of a ratio of thickness to outer diameter and tilt angles of the internal surface flaws of a tubular test object.

The present invention has been completed based on the above-described knowledge of the inventor. That is, the present invention provides a method for performing ultrasonic testing by arranging an ultrasonic probe so as to face an external surface of a tubular test object, wherein a circumferential angle of incidence αi of an ultrasonic wave transmitted from said ultrasonic probe upon said tubular test object and an axial angle of incidence βi of the ultrasonic wave transmitted from said ultrasonic probe upon said tubular test object are set based on a ratio of thickness to outer diameter t/D of said tubular test object so that an internal refraction angle θk calculated from said circumferential angle of incidence αi, said axial angle of incidence βi, and said ratio of thickness to outer diameter t/D of the tubular test object may be not less than 35° and not more than 60°.

According to the present invention, the circumferential angle of incidence αi and the axial angle of incidence βi are set based on the ratio of thickness to outer diameter t/D of the tubular test object so that the internal refraction angle θk may be not less than 35° and not more than 60°. It is thus possible to substantially equalize intensities of echoes reflected by internal surface flaws extending in a direction orthogonal to a propagation direction of ultrasonic waves that is determined by the circumferential angle of incidence αi and the axial angle of incidence βi and, accordingly, detect the internal surface flaws with almost the same detectability irrespective of a ratio of thickness to outer diameter t/D and tilt angles of the internal surface flaws of a tubular test object.

In the present invention, the term "internal refraction angle" means the angle θk formed, on the propagation plane of the ultrasonic wave of the tubular test object P, by a normal L2 of the tubular test object P and the ultrasonic wave U (central line of the ultrasonic wave beam) at a point A on the internal surface of the tubular test object P reached by the ultrasonic wave U (central line of the ultrasonic wave beam) after entering the tubular test object P (See FIG. 3(d)). The term "circumferential angle of incidence" in the present invention means the angle αi formed, on a circumferential cross section of the tubular test object P, by a normal L3 of the tubular test object P and the ultrasonic wave U (central line of the ultrasonic wave beam) at an incident point O of the ultrasonic wave U (central line of the ultrasonic wave beam) (See FIG. 3(b)). Further, the term "axial angle of incidence" in the present invention means the angle βi formed, on an axial cross section of the tubular test object P, by a normal L4 of the tubular test object P and the ultrasonic wave U (central line of the ultrasonic wave beam) at an incident point O of the ultrasonic wave U (central line of the ultrasonic wave beam) (See FIG. 3(c)).

In a case where a direction in which a flaw to be detected extends is known beforehand, preferably said circumferential angle of incidence αi and said axial angle of incidence βi are set so that a propagation direction of an ultrasonic wave made incident upon said tubular test object calculated from said circumferential angle of incidence αi and said axial angle of incidence βi may be substantially orthogonal to an extension direction of a flaw to be detected, and then at least one of said circumferential angle of incidence αi and said axial angle of incidence βi is adjusted so that said internal refraction angle θk may be not less than 35° and not more than 60°.

Preferably, said ultrasonic probe comes in an ultrasonic phased array probe in which a plurality of transducers are arrayed; and by electrically controlling transmission time-shift or reception time-shift of an ultrasonic wave by said plurality of transducers, at least one of said circumferential angle of incidence αi and said axial angle of incidence βi of the ultrasonic wave transmitted to said tubular test object is electrically adjusted.

According to such a preferable configuration, at least one of said circumferential angle of incidence αi and said axial angle of incidence βi can be adjusted easily and with good reproducibility without utilizing a mechanical angle deflection mechanism. Furthermore, it can be adjusted automatically by remote control or in accordance with t/D of the tubular test object and the like.

As described above, although the internal refraction angle θk is calculated from the circumferential angle of incidence αi, the axial angle of incidence βi, and the ratio of thickness to outer diameter t/D of the tubular test object, specifically, said internal refraction angle θk can be calculated by the following Equation (1):

[Eq. 1]

$$\theta k = \cos^{-1}(\cos\theta r \cdot \cos\phi - \sin\theta r \cdot \cos\gamma \cdot \sin\phi) \quad (1)$$

where a propagation angle γ, an external refraction angle θr, and an angle φ are given by the following Equations (2) through (4) respectively:

[Eq. 2]

$$\gamma = \tan^{-1}\left(\frac{\sin\beta i}{\cos\beta i \cdot \sin\alpha i}\right) \quad (2)$$

$$\theta r = \sin^{-1}\left(\{(Vs/Vi)^2 \cdot (\sin^2\beta i + \cos^2\beta i \cdot \sin^2\alpha i)\}^{1/2}\right) \quad (3)$$

$$\phi = \sin^{-1}(k \cdot \sin\theta') - \theta' \quad (4)$$

where, in the above Equation (3), Vs refers to a propagation speed of an ultrasonic wave propagating through the tubular test object and Vi refers to a propagation speed of the ultrasonic wave in a coupling medium that fills a gap between the ultrasonic probe and the tubular test object, k and θ' in the above Equation (4) are given by the following Equations (5) and (6) respectively.

[Eq. 3]

$$k = \frac{1}{1 - 2(t/D)} \quad (5)$$

$$\tan\theta' = \cos\gamma \cdot \tan\theta r \quad (6)$$

In the present invention, the term "propagation angle" means the angle γ formed by the propagation direction (propagation direction viewed from the normal direction of the tangential plane of the tubular test object P including the incident point O of the ultrasonic wave) of the ultrasonic wave (central line of the ultrasonic wave beam) having entered the tubular test object P and a circumferential tangent L of the tubular test object P passing through the incident point O (See FIG. 3(a)). Further, the term "external refraction angle" means the angle θr formed, on a propagation plane of the ultrasonic wave of the tubular test object P, by a normal L1 of the tubular test object P and the ultrasonic wave U (central line of an ultrasonic wave beam) at a point B on the external surface of the tubular test object P reached by the ultrasonic wave U (central line of the ultrasonic wave beam) after entering the tubular test object P (See FIG. 3(d)).

It is to be noted that the external refraction angle θr in the above Equation (1) is a function (in a case where Vs/Vi is set to a constant value) of the circumferential angle of incidence αi and the axial angle of incidence βi as described in Equation (3). The propagation angle γ in the above Equation (1) is a function of the circumferential angle of incidence αi and the axial angle of incidence βi as described in Equation (2). Further, the angle φ in the above Equation (1) is a function of k and θ as described in Equation (4). In this case, k refers to a function of the ratio of thickness to outer diameter t/D of the tubular test object as described in the above Equation (5), and θ' refers to a function of the propagation angle β and the external refraction angle θr as described in the above Equation (6). Accordingly, the angle φ is a function of the circumferential angle of incidence αi, the axial angle of incidence βi, and the ratio of thickness to outer diameter t/D of the tubular test object. Therefore, the internal refraction angle θk given by the above Equation (1) is resultantly a function of the circumferential angle of incidence αi, the axial angle of incidence βi, and the ratio of thickness to outer diameter t/D of the tubular test object.

To solve the problems described above, the present invention also provides a method for performing ultrasonic testing by arranging an ultrasonic probe so as to face an external surface of a tubular test object, wherein an angle of incidence θw of an ultrasonic wave transmitted from said ultrasonic probe upon said tubular test object, and a propagation angle γ of the ultrasonic wave made incident upon said tubular test object are set based on a ratio of thickness to outer diameter t/D of said tubular test object so that an internal refraction angle θk calculated from said angle of incidence θw, said propagation angle γ, and the ratio of thickness to outer diameter t/D of said tubular test object may be not less than 35° and not more than 60°.

According to the present invention, the angle of incidence θw and the propagation angle γ are set in accordance with the ratio of thickness to outer diameter t/D of the tubular test object so that the internal refraction angle θk may be not less than 35° and not more than 60°. It is thus possible to substantially equalize intensities of echoes reflected by the internal surface flaws extending orthogonally to a set propagation direction (propagation angle γ) of an ultrasonic wave and, accordingly, detect the internal surface flaws with almost the same detectability irrespective of a ratio of thickness to outer diameter t/D and tilt angles of the internal surface flaws of the tubular test object.

The term "angle of incidence of the ultrasonic wave upon the tubular test object" in the present invention means the angle θw formed, on the propagation plane of the ultrasonic wave of the tubular test object P, by a normal L3 of the tubular test object P and the ultrasonic wave U (central line of the ultrasonic wave beam) at the incident point O of the ultrasonic wave U (central line of the ultrasonic wave beam) (See FIG. 7(d)). Further, if an angle of incidence θw is determined, an angle of refraction θs is uniquely determined by the Snell's law, so that the expression of "setting angle of incidence θw" in the present invention is of a concept including not only the case of setting the angle of incidence θw literally but also the case of setting the angle of refraction θs.

If a direction in which a flaw to be detected extends is known beforehand, preferably said propagation angle γ is set so that a propagation direction of an ultrasonic wave made incident upon said tubular test object may be substantially orthogonal to an extension direction of a flaw to be detected, and then said angle of incidence θw is adjusted so that said internal refraction angle θk may be not less than 35° and not more than 60°.

As described above, although the internal refraction angle θk is calculated from the angle of incidence θw, the propagation angle γ, and the ratio of thickness to outer diameter t/D of the tubular test object, specifically, said internal refraction angle θk can be calculated by the following Equation (1):

[Eq. 4]

$$\theta k = \cos^{-1}(\cos\theta r \cdot \cos\phi - \sin\theta r \cdot \cos\gamma \cdot \sin\phi) \quad (1)$$

where an external refraction angle θr and an angle φ in the above Equation (1) are given by the following Equations (7) and (4) respectively:

[Eq. 5]

$$\sin\theta r = Vs/Vi \cdot \sin\theta w \quad (7)$$

$$\phi = \sin^{-1}(k \cdot \sin\theta') - \theta' \quad (4)$$

where, in the above Equation (7), Vs refers to a propagation speed of an ultrasonic wave propagating through the tubular test object and Vi refers to a propagation speed of the ultrasonic wave in a coupling medium that fills a gap between the ultrasonic probe and the tubular test object, and k and θ' in the above Equation (4) are given by the following Equations (5) and (6) respectively.

[Eq. 6]

$$k = \frac{1}{1 - 2(t/D)} \quad (5)$$

$$\tan\theta' = \cos\gamma \cdot \tan\theta r \quad (6)$$

It is to be noted that the external refraction angle θr in the above Equation (1) is a function (in a case where Vs/Vi is set to a constant value) of the angle of incidence θw as described in Equation (7). The angle φ in the above Equation (1) is a function of k and θ' as described in Equation (4). It is to be noted that k refers to a function of the ratio of thickness to outer diameter t/D of the tubular test object as described in the above Equation (5), and θ' refers to a function of the propagation angle γ and the external refraction angle θr as described in the above Equation (6). Accordingly, the angle φ is a function of the angle of incidence θw, the propagation angle γ, and the ratio of thickness to outer diameter t/D of the tubular test object. Therefore, the internal refraction angle θk given by the above Equation (1) is a function of the angle of incidence θw, the propagation angle γ, and the ratio of thickness to outer diameter t/D of the tubular test object.

Further, to solve the problems above, the present invention also provides a method for manufacturing a seamless steel pipe, comprising: a first step of piercing a billet to manufacture a seamless steel pipe; and a second step of detecting a flaw in the seamless steel pipe manufactured by said first step, by using the ultrasonic testing method.

BEST MODE FOR CARRYING OUT THE INVENTION

The following will describe embodiments of the present invention in an example where a tubular test object is a pipe such as a steel pipe with reference to the accompanying drawings appropriately.

First Embodiment

Figure 1:
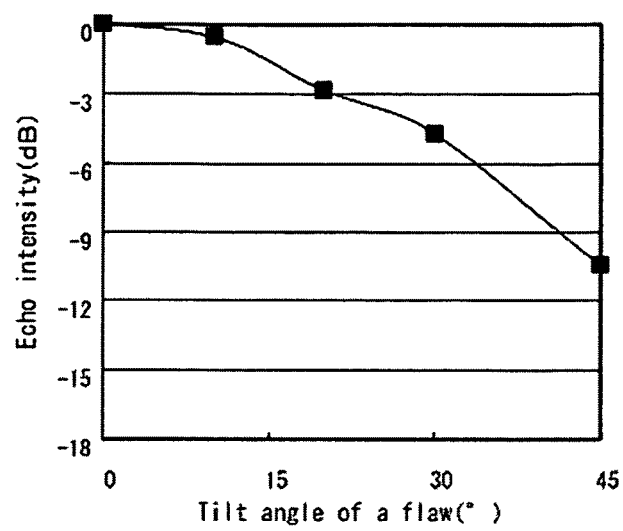
FIG. 1 is a graph showing one example of a relationship between a tilt angle of a tilted flaw and an echo intensity with a flaw detection method applying a conventional ultrasonic phased array probe.
Figure 2:
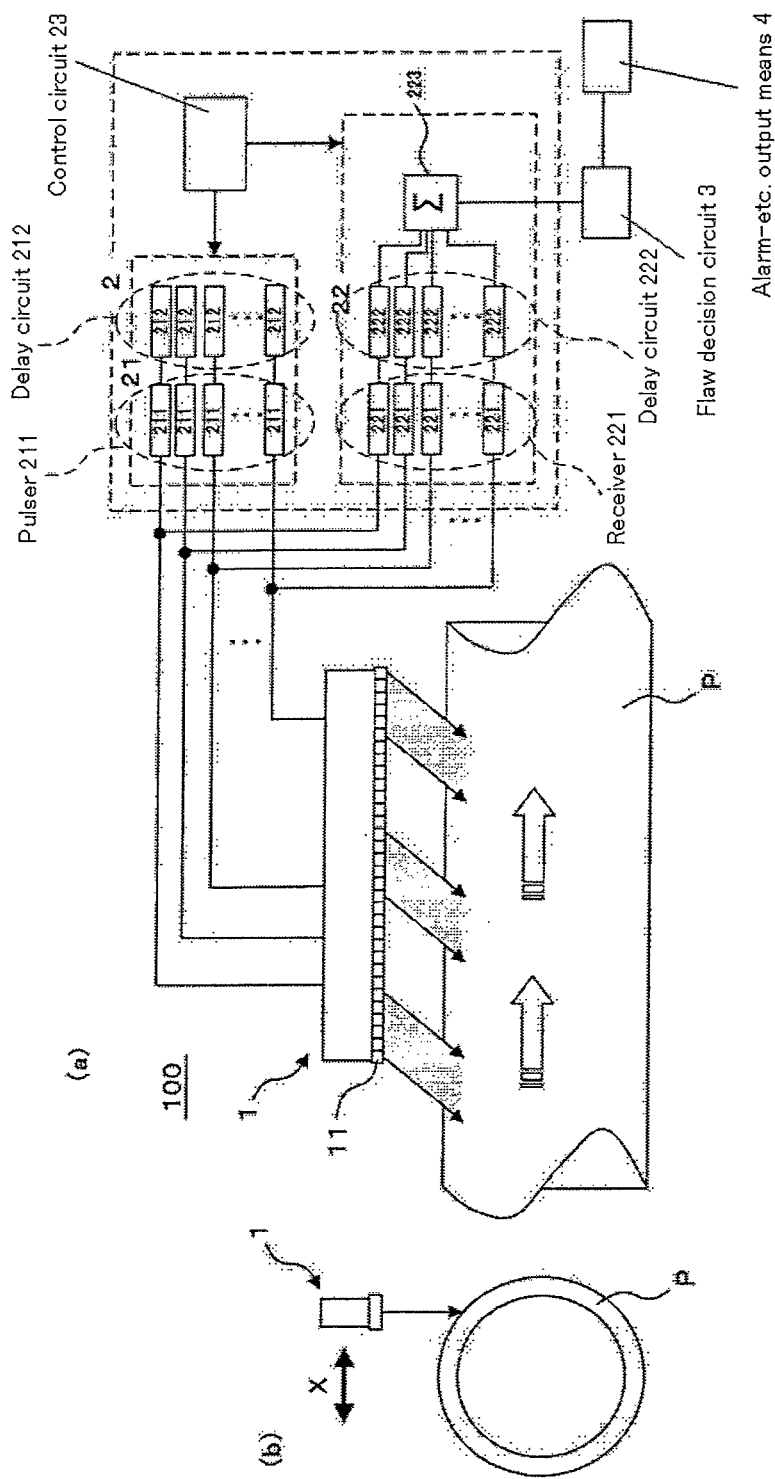
FIG. 2 is a schematic diagram showing an outlined configuration of an ultrasonic testing apparatus according to a first embodiment of the present invention.
Figure 3:
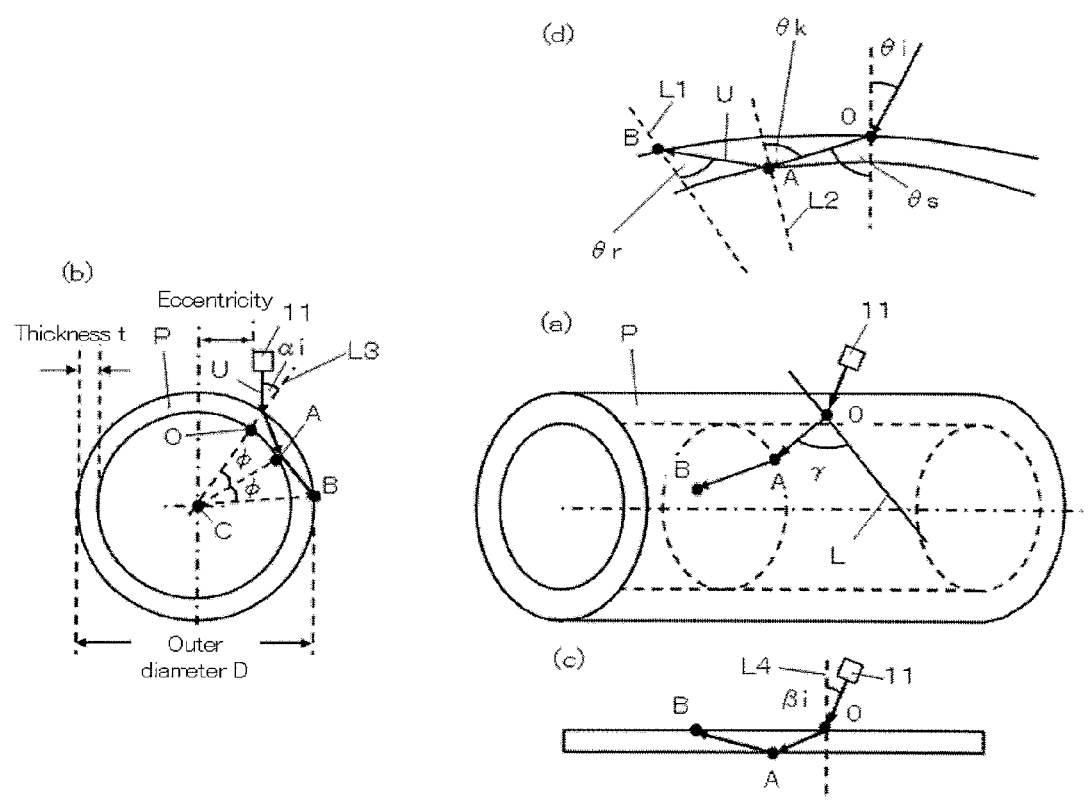
FIG. 3 is an explanatory illustration showing propagation behaviors of an ultrasonic wave in the ultrasonic testing apparatus shown in FIG. 2.

FIG. 2 is a schematic diagram showing an outlined configuration of an ultrasonic testing apparatus for performing an ultrasonic testing according to the first embodiment of the present invention, of which FIG. 2A is a front view and FIG. 2B is a side view. FIG. 3 is an explanatory illustration showing propagation behaviors of an ultrasonic wave in the ultrasonic testing apparatus shown in FIG. 2, of which FIG. 3A is a perspective view, FIG. 3B is a pipe-circumferential cross-sectional view, FIG. 3C is a pipe-axial cross-sectional view, and FIG. 3D is a cross-sectional view along a plane of propagation of ultrasonic waves (i.e., plane including points O, A, and B shown in FIG. 3A). As shown in FIG. 2, an ultrasonic testing apparatus 100 according to the present embodiment comprises an ultrasonic phased array probe 1 in which a plurality of (128 in the present embodiment) strip transducers (which each have 0.75 mm by 10 mm and operate on an oscillation frequency of 5 MHz in the present embodiment) 11 are arrayed straightly, and transmission/reception control means 2 for controlling transmission and reception of ultrasonic waves by the ultrasonic probe 1. The ultrasonic testing apparatus 100 according to the present embodiment further comprises a flaw decision circuit 3 for detecting a flaw present in a pipe P by comparing an amplitude of a reflected echo from the pipe P (more specifically, reflected echo synthesized by a waveform synthesis circuit 223 described later) to a predetermined threshold value, and alarm-etc. output means 4 for outputting a predetermined alarm etc. if a flaw is detected by the flaw decision circuit 3.

The ultrasonic probe 1 is arranged so as to face an external surface of the pipe P via a coupling medium (water in the present embodiment) so that the transducers 11 may be arrayed along an axial direction of the pipe P. The ultrasonic probe 1 can be moved horizontally (in a direction indicated by arrow X in FIG. 2B) and fixed to an arbitrary position by using a positioning mechanism (not shown) which is constituted of a ball screw etc. A circumferential angle of incidence αi of an ultrasonic wave upon the pipe P (angle formed by a normal L3 at point O of the pipe P and an ultrasonic wave beam U: see FIG. 3B) is determined based on a horizontal position (an eccentricity with respect to an axial center of the pipe P in the pipe-circumferential cross-section) of the ultrasonic probe 1 that is set by the positioning mechanism.

The transmission/reception control means 2 according to the present embodiment comprises a transmission circuit 21, a reception circuit 22, and a control circuit 23. The transmission circuit 21 comprises a pulser 211 connected to each of the transducers 11 to supply it with a pulse signal so that it may transmit an ultrasonic wave, and a delay circuit 212 for setting a delay time (transmission delay time) of the pulse signal to be supplied from each of the pulsers 211 to each of the transducers 11. The reception circuit 22 comprises a receiver 221 connected to each of the transducers 11 to amplify an reflected echo received by each of the transducers 11, a delay circuit 222 for setting a delay time (reception delay time) of the reflected echo amplified by each of the receivers 221, and a waveform synthesis circuit 223 for synthesizing the reflected echo to which a delay time is set by each of the delay circuits 222. The control circuit 23 selects one of the plurality of arrayed transducers 11 that is scheduled to transmit or receive an ultrasonic wave and determines a delay time to be set by the delay circuit 212 or the delay circuit 222 corresponding to the selected each of the transducers 11.

In the transmission/reception control means 2 having the configuration as described above, the delay circuit 212 sets a predetermined transmission delay time, to enable changing a propagation direction of an ultrasonic wave transmitted from the ultrasonic probe 1. Subsequently, a predetermined reception delay time (which is generally the same as the delay time set by the delay circuit 212) is set by the delay circuit 222 to the reflected echo amplified by the receiver 221, and then undergoes synthesis at the waveform synthesis circuit 223, thereby enabling selectively amplifying an ultrasonic wave that has propagated over in a specific direction.

In other words, delay control by the delay circuits 212 and 222 according to the present embodiment enables performing ultrasonic electric deflected scanning in the direction (axial direction of the pipe P) in which the transducers 11 are arrayed. That is, through delay control by the delay circuits 212 and 222, an axial angle of incidence βi of an ultrasonic wave upon the pipe P (angle formed by a normal L4 at point O on the pipe P and the ultrasonic wave beam U in the pipe-axial cross-section: see FIG. 3C) is determined.

More specifically, the ultrasonic testing apparatus 100 according to the present embodiment has such a configuration that a transmission delay time and a reception delay time which are calculated from a propagation speed of an ultrasonic wave (ultrasonic longitudinal wave) in a coupling medium (water), a propagation speed of an ultrasonic wave (ultrasonic shear wave) in the pipe P, an array pitch of the transducers 11, and the like are set to a transducer group (transducer group of the 16 transducers in the present embodiment) of a predetermined number of the transducers 11 among the plurality of transducers 11 constituting the ultrasonic probe 1, thereby transmitting and receiving the ultrasonic wave deflected by the axial angle of incidence βi so that flaws may be detected. When one transducer group finished flaw detection, the other transducer groups to be selected are sequentially switched to perform electric scanning, thereby improving a flaw detection speed. In this case, if such a configuration is employed that ultrasonic waves may be transmitted and received simultaneously by the plurality of transducer groups (three transducer groups in the present embodiment), a speed of electric scanning itself can be improved. Further, by transmitting and receiving ultrasonic wave having different axial angles of incidence βi by the selected plurality of transducer groups respectively, it is possible to simultaneously detect a plurality of flaws having different tilt angles. It is to be noted that the present embodiment has realized ultrasonic testing over a total length of the pipe P by spirally feeding the pipe P axially.

It is to be noted that the ultrasonic testing apparatus 100 according to the present embodiment features that a circumferential angle of incidence αi and an axial angle of incidence βi are set based on a ratio of thickness to outer diameter t/D of the pipe P so that an internal refraction angle θk described later may be not less than 35° and not more than 60°. Reasons for this are described below more specifically with reference to FIG. 3 appropriately.

As shown in FIG. 3, ultrasonic waves transmitted from each of the transducers 11 of the ultrasonic probe 1 are supposed to enter the pipe P at point O on its external surface, reflected at point A on an internal surface of the pipe P, and reach point B on the external surface of the pipe P. Further, it is supposed that an angle (propagation angle) formed by a propagation direction of the ultrasonic wave that has entered through point O (propagation direction as viewed from a direction of a normal of a tangential plane of the pipe P including the point of incidence O) and a circumferential tangent L of the pipe P passing through the point of incidence O is to be γ (hereinafter referred to as "propagation direction γ" appropriately), an external refraction angle at point B (angle formed by a normal L1 at point B on the pipe P and the ultrasonic wave beam U on an ultrasonic wave propagation plane shown in FIG. 3(d)) is θr, and an internal refraction angle at point A (angle formed by a normal L2 at point A on the pipe P and the ultrasonic wave beam U on the ultrasonic wave propagation plane shown in FIG. 3(d)) is θk, then θk, γ, and θr are given by the following Equations (1) through (3) respectively:

[Eq. 7]

$$\theta k = \cos^{-1}(\cos\theta r \cdot \cos\phi - \sin\theta r \cdot \cos\gamma \cdot \sin\phi) \quad (1)$$

$$\gamma = \tan^{-1}\left(\frac{\sin\beta i}{\cos\beta i \cdot \sin\alpha i}\right) \quad (2)$$

$$\theta r = \sin^{-1}\left(\{(Vs/Vi)^2 \cdot (\sin^2\beta i + \cos^2\beta i \cdot \sin^2\alpha i)\}^{1/2}\right) \quad (3)$$

It is to be noted that Vs in the above Equation (3) refers to a propagation speed of an ultrasonic wave propagating through the pipe P and Vi refers to a propagation speed of the ultrasonic wave in a coupling medium that fills a gap between the transducers 11 and the pipe P. Further, in the above Equation (1), φ refers to an angle formed by a straight line passing through a center C of the pipe and point O and a straight line passing through the center C of the pipe and point A (which is equal to an angle formed by a straight line passing through the center C of the pipe and point A and a straight line passing through the center C of the pipe and point B) in the pipe-axial cross-section shown in FIG. 3B, and given by the following Equation (4):

[Eq. 8]

$$\varphi = \sin^{-1}(k \cdot \sin \theta') - \theta' \quad (4)$$

In the above Equation (4), k and θ' are given by the following Equations (5) and (6) respectively:

[Eq. 9]

$$k = \frac{1}{1 - 2(t/D)} \quad (5)$$

$$\tan\theta' = \cos\gamma \cdot \tan\theta r \quad (6)$$

As can be seen from the above Equations (2) and (3), the propagation direction γ and the external refraction angle θr of the ultrasonic wave are each a function of a circumferential angle of incidence αi of an ultrasonic wave upon the pipe P and an axial angle of incidence βi of the ultrasonic wave upon the pipe P that are determined by an eccentricity of the ultrasonic probe 1. Further, the internal refraction angle θk given in the above Equation (1) is a function of the circumferential angle of incidence αi, the axial angle of incidence βi, and the ratio of thickness to outer diameter t/D of the pipe P as derived from the above Equations (2) through (6).

It is to be noted that as described above, according to the method disclosed in Patent Literature 2, under such a condition as to provide a constant eccentricity at the time of arranging the ultrasonic probe in condition where it is decentralized from the axial center of the pipe P (that is, to provide a constant circumferential angle of incidence αi upon the pipe P that is determined based on an eccentricity), only a tilt angle of an ultrasonic wave with respect to the axial direction of the pipe P is changed (only the axial angle of incidence βi is changed) so that a propagation direction of the ultrasonic wave may be orthogonal to a direction in which a tilted flaw extends. In this case, if only the axial angle of incidence βi is changed as derived from the above Equations (1) and (3), the external refraction angle θr and the internal refraction angle θk each change as the axial angle of incidence βi changes, so that as described above, an echo intensity changes with the tilt angle of the tilted flaw, thus leading to a change in flaw detectability.

Figure 4:
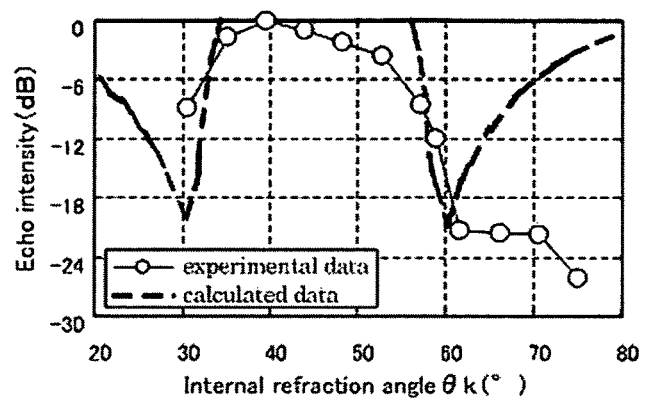
FIG. 4 is a graph showing one example of a relationship between an internal refraction angle and an echo intensity at an internal surface flaw.

FIG. 4 shows one example of an intensity of an echo reflected by an internal surface flaw (having a depth of 0.5 mm and a length of 25 mm) in a case where the internal refraction angle θk is changed in a range between 30° and 75°, both inclusive, in a state where an extending direction of the internal surface flaw is orthogonal to the propagation direction γ of an ultrasonic wave transmitted from the ultrasonic probe. It is to be noted that such a change in echo intensity as shown in FIG. 4 has the same tendency irrespective of the propagation direction γ of ultrasonic waves. As shown in FIG. 4, in a range of the internal refraction angle θk between 35° and 55°, both inclusive, the echo intensity stays substantially constant; however, in a range of θk beyond 55°, the echo intensity decreases monotonously, until it has a value not more than −12 dB with respect to its peak value of the echo intensity (when θk≅40°) when θk=60°. It is to be noted that experimental data shown in FIG. 4 and calculated data obtained by numeral calculations differ in a range where the angle of refraction θk exceeds 60°. This phenomenon is considered to be caused by a fact that as the internal refraction angle θk increases, an angle of refraction θs of ultrasonic waves on the pipe P (angle formed by a normal at point of incidence O on the pipe P and an ultrasonic wave beam U on an ultrasonic wave propagation plane shown in FIG. 3(d)) also increases, so that as a result, in actual experiments, a reciprocating transmission factor at an interface between a coupling medium and the pipe P decreases or the waves are attenuated more as they propagate through the pipe P.

Amplification by the receiver 221 can compensate for a decrease of only a maximum value of −12 dB or so actually in echo intensity caused by a change in angle of refraction θk. Therefore, as can be seen from FIG. 4, it is necessary to set such a condition that the internal refraction angle θk may be 60° or less, so as to obtain at least −12 dB of an echo intensity as compared to its peak value.

On the other hand, it is already known that if the internal refraction angle θk is about 30° or less, when a traversal ultrasonic wave that has reached an internal surface of the pipe P is reflected, at least 50% of its energy is converted from a traversal wave mode to a longitudinal wave mode. It causes a problem that this mode conversion decreases an intensity of an ultrasonic shear wave propagating through the pipe P, thus resulting in a decrease in detectability of 1.0-skip external surface flaws. To avoid such a problem and in consideration of a spread in ultrasonic wave beam of about ±2 to 5°, it is necessary to set such a condition that the internal refraction angle θk may be 35° or larger, to prevent conversion to the ultrasonic shear wave mode when the wave is reflected at the internal surface of the pipe P.

For the reasons described above, in the ultrasonic testing apparatus 100 according to the present embodiment, the circumferential angle of incidence αi and the axial angle of incidence βi are set based on the ratio of thickness to outer diameter t/D of the pipe P so that the internal refraction angle θk may be not less than 35° and not more than 60°, both inclusive (preferably not less than 35° and not more than 55°, both inclusive, where the echo intensity changes less). It is thus possible to substantially equalize reflected echo intensities at internal surface flaws and hence detect the internal surface flaws with almost the same detectability, irrespective of the ratio of thickness to outer diameter t/D and tilt angles of the internal surface flaws of the pipe P.

It is to be noted that in a case where an extension direction of an internal surface flaw to be detected is known already, it has only to set the circumferential angle of incidence αi and the axial angle of incidence βi so that the propagation direction γ of an ultrasonic wave made incident upon the pipe P may be substantially orthogonal to the extension direction of the flaw to be detected, and then adjust at least one of the circumferential angle of incidence αi and the axial angle of incidence βi so that the internal refraction angle θk may be not less than 35° and not more than 60°.

Further, if a configuration for changing an amplitude of the receiver 221 based on a change in internal refraction angle θk in a range between 35° and 60°, both inclusive, is employed, it is preferable in that reflected echo intensities at the internal surface flaws can be equalized even more substantially and hence detectabilities of the internal surface flaws can be equalized even more substantially.

Table 1 shows results of calculations of the propagation angle γ, the external refraction angle θr, and the internal refraction angle θk of an ultrasonic wave in a case where the circumferential angle of incidence αi and the axial angle of incidence βi in the ultrasonic testing apparatus 100 are set to a variety of values for the pipe P having an outer diameter of 190 mm and a thickness of 11 mm (t/D≅5.8%). In these calculations, the above Equations (1) through (6) were used. Further, in Equation (3), Vs=3200 m/sec (propagation speed of an ultrasonic shear wave through the steel pipe) and Vi=1500 m/sec (propagation speed of ultrasonic longitudinal waves in water).

TABLE 1

|   | eccentricity (mm) | circumferential angle of incidence αi (°) | axial angle of incidence βi (°) | propagation angle γ (°) | external refraction angle θr (°) | internal refraction angle θk (°) |
|---|---|---|---|---|---|---|
| A | 26 | 16 | 0 | 0 | 36 | 42 |
| B | 24 | 15 | 6 | 22 | 36 | 41 |
| C | 20 | 12 | 12 | 45 | 39 | 42 |
| D | 25 | 15 | 0 | 0 | 35 | 40 |
| E | 25 | 15 | 6 | 22 | 38 | 43 |
| F | 25 | 15 | 15 | 45 | 51 | 56 |
| G | 11 | 7 | 16 | 67 | 40 | 41 |
| H | 7 | 4 | 19 | 78 | 46 | 46 |

In the case of performing ultrasonic testing on an internal surface flaw, to obtain equal flaw echoes (echoes reflected by internal surface flaws) irrespective of tilt angles (=propagation angle γ of an ultrasonic wave) of the internal surface flaws (that is, to obtain the equal internal refraction angle θk), it is ideal from a viewpoint of stability of flaw detection results to adjust and set an eccentricity (circumferential angle of incidence αi) and the axial angle of incidence βi for each of tilt angles of the internal surface flaws, for example, as shown in conditions A, B, and C in Table 1. However, this approach has drawbacks of troublesome setting and a necessity of preparing a plurality of the ultrasonic probes 1 to which different eccentricities are set in a case where internal surface flaws having different tilt angles are to be detected simultaneously.

On the other hand, if the tilt angles of the internal surface flaws are in a range between 0° and 45°, both inclusive (that is, the propagation angle γ of an ultrasonic wave is in a range between 0° and 45°, both inclusive), even if eccentricities of the ultrasonic probes 1 are set constant, it is possible to set the internal refraction angle θk in a range between 40° and 56°, both inclusive, by appropriately setting the eccentricity (circumferential angle of incidence αi) and the axial angle of incidence βi as shown in the conditions D, E, and F in Table 1. As far as the internal refraction angle θk changes in such a range, the echo intensity at the internal surface flaws changes by as much as about 10 dB as shown in FIG. 4 above described, so that by employing a configuration for changing an amplification of the receiver 221 based on the propagation angle γ of the ultrasonic wave (based on the tilt angle of the internal surface flaw), almost the same detectability can be given for the internal surface flaws having any tilt angles in the range between 0° and 45°, both inclusive.

Further, as described above, in a case were a configuration for simultaneously transmitting and receiving ultrasonic waves by using three transducer groups, by setting the conditions D, E, and F in Table 1 to the first, second, and third transducer groups respectively, it is possible to simultaneously detect internal surface flaws having tilt angles of 0°, 22°, and 45° with the single ultrasonic probe 1.

Table 2 shows results of calculations of the propagation angle γ, the external refraction angle θr, and the internal refraction angle θk of an ultrasonic wave in a case where the circumferential angle of incidence αi and the axial angle of incidence βi in the ultrasonic testing apparatus 100 are set to a variety of values for the pipe P having an outer diameter of 160 mm and a thickness of 28 mm (t/D≅18%). It is to be noted that as in the case of Table 1, in these calculations, Equations (1) through (6) described above were used. Further, in Equation (3), Vs=3200 m/sec (propagation speed of an ultrasonic shear wave through the steel pipe) and Vi=1500 m/sec (propagation speed of ultrasonic longitudinal waves in water).

TABLE 2

|   | eccentricity (mm) | circumferential angle of incidence αi (°) | axial angle of incidence βi (°) | propagation angle γ (°) | external refraction angle θr (°) | internal refraction angle θk (°) |
|---|---|---|---|---|---|---|
| A | 19 | 12 | 0 | 0 | 26 | 41 |
| B | 19 | 12 | 5 | 22 | 28 | 43 |
| C | 19 | 12 | 12 | 45 | 37 | 51 |
| D | 11 | 7 | 16 | 67 | 39 | 43 |
| E | 7 | 4 | 19 | 78 | 46 | 48 |

As shown in conditions A, B, and C in Table 2, values of an eccentricity (circumferential angle of incidence αi) and the axial angle of incidence βi are different from those for the conditions D, E, and F in Table 1; however, as far as, by appropriately setting them respectively, the tilt angles of the internal surface flaws fall in a range between 0° and 45°, both inclusive (that is, the propagation angle γ of an ultrasonic wave falls in a range between 0° and 45°, both inclusive), even if eccentricities of the ultrasonic probes 1 are set constant, it is possible to set the internal refraction angle θk in a range between 41° and 51°, both inclusive. Therefore, by employing a configuration for changing an amplification of the receiver 221 based on the propagation angle γ of the ultrasonic wave (based on the tilt angle of the internal surface flaw), almost the same detectability can be given for the internal surface flaws having any tilt angles in the range between 0° and 45°, both inclusive.

However, under any conditions given in Tables 1 and 2, if the tilt angle of an internal surface flaw (propagation angle γ of the ultrasonic wave) takes a large value of 67° (condition G in Table 1 or condition D in Table 2) or 78° (condition H in Table 1 or condition E in Table 2), it is necessary to adjust and set an eccentricity (circumferential angle of incidence αi) and an axial angle of incidence βi for each of the tilt angles of the internal surface flaws.

Second Embodiment

Figure 5:
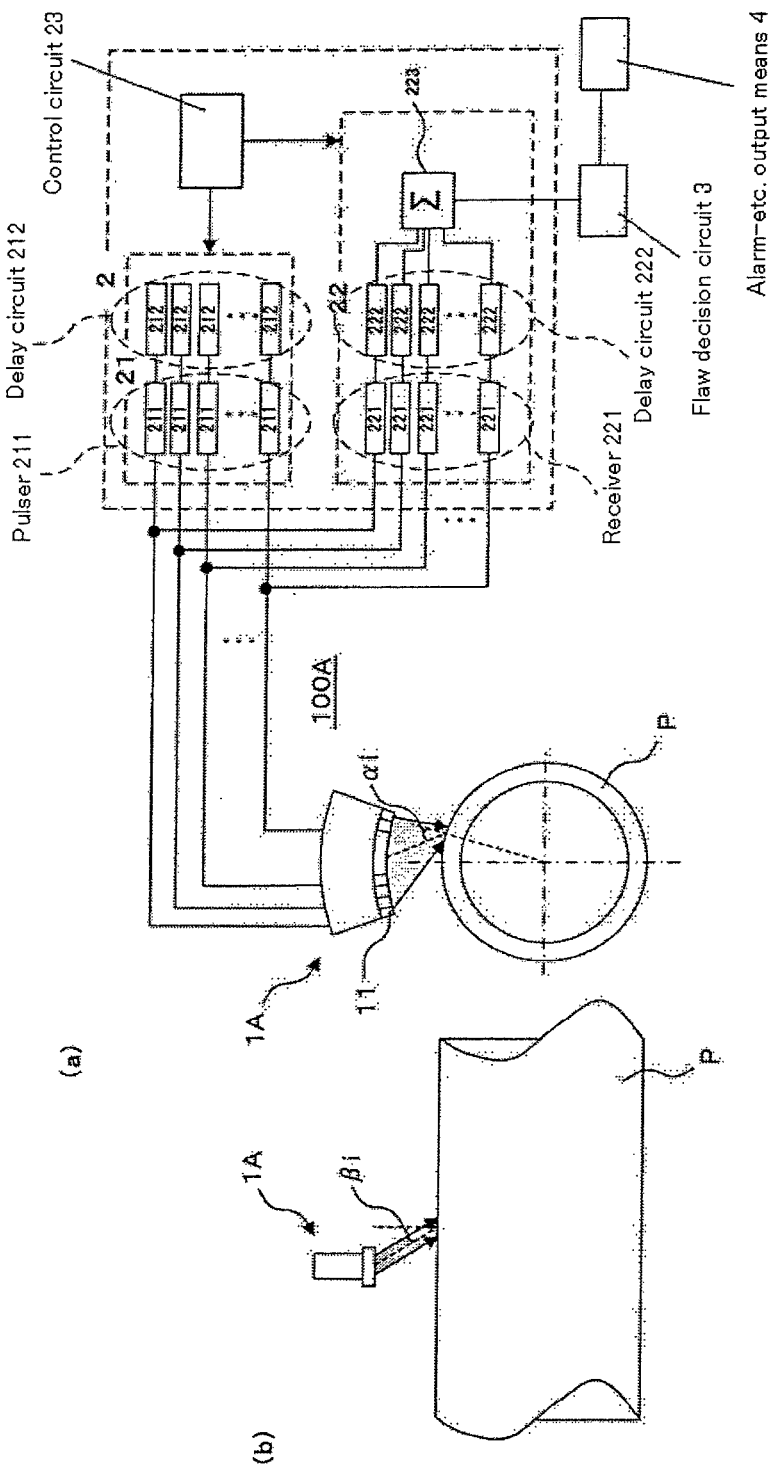
FIG. 5 is a schematic diagram showing an outlined configuration of an ultrasonic testing apparatus according to a second embodiment of the present invention.

FIG. 5 is a schematic diagram showing an outlined configuration of an ultrasonic testing apparatus for performing an ultrasonic testing according to the second embodiment of the present invention, of which FIG. 5A is a side view and FIG. 5B is a front view. As shown in FIG. 5, an ultrasonic testing apparatus 100A according to the present embodiment comprises an ultrasonic phased array probe 1A in which a plurality (32 in the present embodiment) of strip transducers (which each have 0.75 mm by 10 mm and operate on an oscillation frequency of 5 MHz) 11 are arrayed in a shape of concentric arcs of the pipe P, and transmission/reception control means 2 for controlling transmission and reception of ultrasonic waves by the ultrasonic probe 1A. Like the ultrasonic testing apparatus 100 according to the first embodiment, also the ultrasonic testing apparatus 100A according to the present embodiment comprises a flaw decision circuit 3 for detecting a flaw present in a pipe P by comparing an amplitude of a reflected echo from the pipe P to a predetermined threshold value, and alarm-etc. output means 4 for outputting a predetermined alarm etc. if a flaw is detected by the flaw decision circuit 3.

The ultrasonic probes 1A are arranged so as to face an external surface of the pipe P via a coupling medium (water in the present embodiment) so that the arrayed direction of the transducers 11 is along the circumferential direction of the pipe P. In this configuration, the transducers 11 are each arranged as tilted in an axial direction of the pipe P so that a transmitted ultrasonic wave may have a predetermined axial angle of incidence $\beta i$ (17° in the present embodiment). Therefore, for the ultrasonic probe 1A according to the present embodiment, the axial angle of incidence $\beta i$ of an ultrasonic wave to be sent to the pipe P takes a fixed value determined by a tilt of the transducers 11.

The transmission/reception control means 2 according to the present embodiment has the same configuration as that according to the first embodiment and so is capable of ultrasonic electric deflected scanning in a direction in which the transducers 11 are arrayed (circumference direction of the pipe P). That is, a circumferential angle of incidence $\alpha i$ of an ultrasonic wave upon the pipe P is determined through delay control by delay circuits 212 and 222.

More specifically, the ultrasonic testing apparatus 100A according to the present embodiment has such a configuration that a transmission delay time and a reception delay time which are calculated from a propagation speed of an ultrasonic wave (ultrasonic longitudinal wave) in a coupling medium (water), a propagation speed of an ultrasonic wave (ultrasonic shear wave) in the pipe P, an array pitch of the transducers 11, and the like, are set to the 32 transducers of the ultrasonic probe 1A, thereby transmitting and receiving the ultrasonic wave deflected by the circumferential angle of incidence $\alpha i$ so that flaws may be detected. Then, by changing settings of the transmission delay time and the reception delay time to detect flaws as speedily changing a circumferential angle of incidence $\alpha i$, it is possible to sequentially detect the flaws having different tilt angles. It is to be noted that the present embodiment has realized ultrasonic testing over a total length of the pipe P by spirally feeding the pipe P axially.

Like that according to the first embodiment, the ultrasonic testing apparatus 100A according to the present embodiment features that the circumferential angle of incidence $\alpha i$ and the axial angle of incidence $\beta i$ are set based on a ratio of thickness to outer diameter t/D of the pipe P so that an internal refraction angle $\theta k$ given in the above Equation (1) may be not less than 35° and not more than 60°. It is thus possible to substantially equalize reflected echo intensities at internal surface flaws and hence detect the internal surface flaws with almost the same detectability, irrespective of the ratio of thickness to outer diameter t/D and tilt angles of the internal surface flaws of the pipe P.

Like the first embodiment, in the present embodiment also, if a configuration for changing an amplitude of a receiver 221 based on a change in internal refraction angle $\theta k$ in a range between 35° and 60°, both inclusive, is employed, it is preferable in that reflected echo intensities at the internal surface flaws can be equalized even more and hence detectabilities of the internal surface flaws can be equalized even more.

Table 3 shows results of calculations of a propagation angle $\gamma$, an external refraction angle $\theta r$, and an internal refraction angle $\theta k$ of an ultrasonic wave in a case where the circumferential angle of incidence $\alpha i$ is set to a variety of values (in condition where the axial angle of incidence $\beta i$ is fixed to 17°) in the ultrasonic testing apparatus 100A for the pipe P having an outer diameter of 190 mm and a thickness of 11 mm (t/D≅5.8%). In these calculations, the Equations (1) through (6) described above were used. Further, in Equation (3), Vs=3200 m/sec (propagation speed of an ultrasonic shear wave through the steel pipe) and Vi=1500 m/sec (propagation speed of ultrasonic longitudinal waves in water).

TABLE 3

| | circumferential angle of incidence $\alpha i$ (°) | axial angle of incidence $\beta i$ (°) | propagation angle $\gamma$ (°) | external refraction angle $\theta r$ (°) | internal refraction angle $\theta k$ (°) |
|---|---|---|---|---|---|
| A | 0 | 17 | 90 | 39 | 39 |
| B | 4 | 17 | 78 | 40 | 40 |
| C | 7 | 17 | 67 | 43 | 44 |
| D | 15 | 17 | 50 | 55 | 60 |

As shown in Table 3, by electrically changing the circumferential angle of incidence $\alpha i$ in a range between 0° and 15°, both inclusive, in condition where the axial angle of incidence $\beta i$ is fixed to 17°, it is possible to change the propagation angle $\gamma$ of ultrasonic waves in a range between 50° and 90°, both inclusive, while keeping the internal refraction angle $\theta k$ in a range between 39° and 60°, both inclusive. Therefore, by employing a configuration for changing an amplification of the receiver 221 based on the propagation angle $\gamma$ of the ultrasonic waves (based on the tilt angle of the internal surface flaw), almost the same detectability can be given for the internal surface flaws having any tilt angles in the range between 50° and 90°, both inclusive.

Third Embodiment

An ultrasonic testing apparatus according to the present embodiment has a configuration that the ultrasonic testing apparatus 100 according to the first embodiment shown in FIG. 2 and the ultrasonic testing apparatus 100A according to the second embodiment shown in FIG. 5 are combined. More specifically, in this configuration, the ultrasonic probe 1 in the ultrasonic testing apparatus 100 and the ultrasonic probe 1A in the ultrasonic testing apparatus 100A are provided side by side in a circumference direction of a pipe P or an axial direction thereof. It is to be noted that the transmission/reception control means 2 for controlling transmission and reception of ultrasonic waves by the ultrasonic probe may be provided separately for the ultrasonic probes 1 and 1A or may be shared in use by the ultrasonic probes 1 and 1A.

As described above, in the ultrasonic testing apparatus 100 according to the first embodiment, it is possible to change an axial angle of incidence βi in condition where an eccentricity of the ultrasonic probe 1 is fixed (a circumferential angle of incidence αi is fixed) as shown in conditions D, E, and F in Table 1 or conditions A, B, and C in Table 2, thereby detecting substantially equally also internal surface flaws having any tilt angles in a range between 0° and 45°, both inclusive.

On the other hand, in the ultrasonic testing apparatus 100A according to the second embodiment, it is possible to change the circumferential angle of incidence αi in condition where the axial angle of incidence βi is fixed as shown in Table 3, thereby detecting substantially equally also internal surface flaws having any tilt angles in a range between 50° and 90°, both inclusive.

Therefore, the ultrasonic testing apparatus according to the present embodiment made by combining the ultrasonic testing apparatus 100 and the ultrasonic testing apparatus 100A, it is possible to detect substantially equally also internal surface flaws having any tilt angles in a range between 0° and 90°, both inclusive. Further, it is necessary only to electrically change the circumferential angle of incidence αi of the ultrasonic testing apparatus 100A and the axial angle of incidence βi of the ultrasonic testing apparatus 100 by means of delay control, to eliminate mechanical adjustment of the circumferential angle of incidence αi and the axial angle of incidence βi, so that the flaw detection condition can be set extremely easily to improve an efficiency of flaw detection.

It is to be noted that by employing such a configuration of the ultrasonic testing apparatus according to the present embodiment that the ultrasonic probes 1 and the ultrasonic probes 1A are provided by as many as two each, it is possible to detect substantially equally also internal surface flaws having any tilt angles in a range between 0° and 360°, both inclusive, by use of the following arrangement, for example. That is, the respective ultrasonic probes 1 are arranged so that they may have opposite signs of an eccentricity (circumferential angle of incidence αi) and also subject to delay control so that they may have opposite signs of a range in which the axial angle of incidence βi of each of the ultrasonic probes 1 is changed. On the other hand, the ultrasonic probes 1A are arranged so that they may have opposite signs of the axial angle of incidence βi and also subject to delay control so that they may have opposite signs of a range in which the circumferential angle of incidence βi of each of the ultrasonic probes 1A is changed. It is thus possible to detect substantially equally internal surface flaws having any tilt angles in a range between 0° and 360°, both inclusive.

Further, a variant of the ultrasonic testing apparatus according to the present embodiment may employ such a configuration as to comprise a two-dimensional ultrasonic phased array probe in which minute transducers are arrayed in axis and circumference directions of the pipe P. Also in such a configuration, it is possible to detect substantially equally also internal surface flaws having any tilt angles in a range between 0° and 360°, both inclusive, by employing a configuration that the circumferential angle of incidence αi and the axial angle of incidence βi are adjusted by conducting delay control on each of the transducers so that an internal refraction angle θk may be not less than 35° and not more than 60°, both inclusive, to change an amplification of a receiver 221 based on the propagation angle γ of the ultrasonic wave (based on the tilt angle of the internal surface flaw).

Fourth Embodiment

Figure 6:
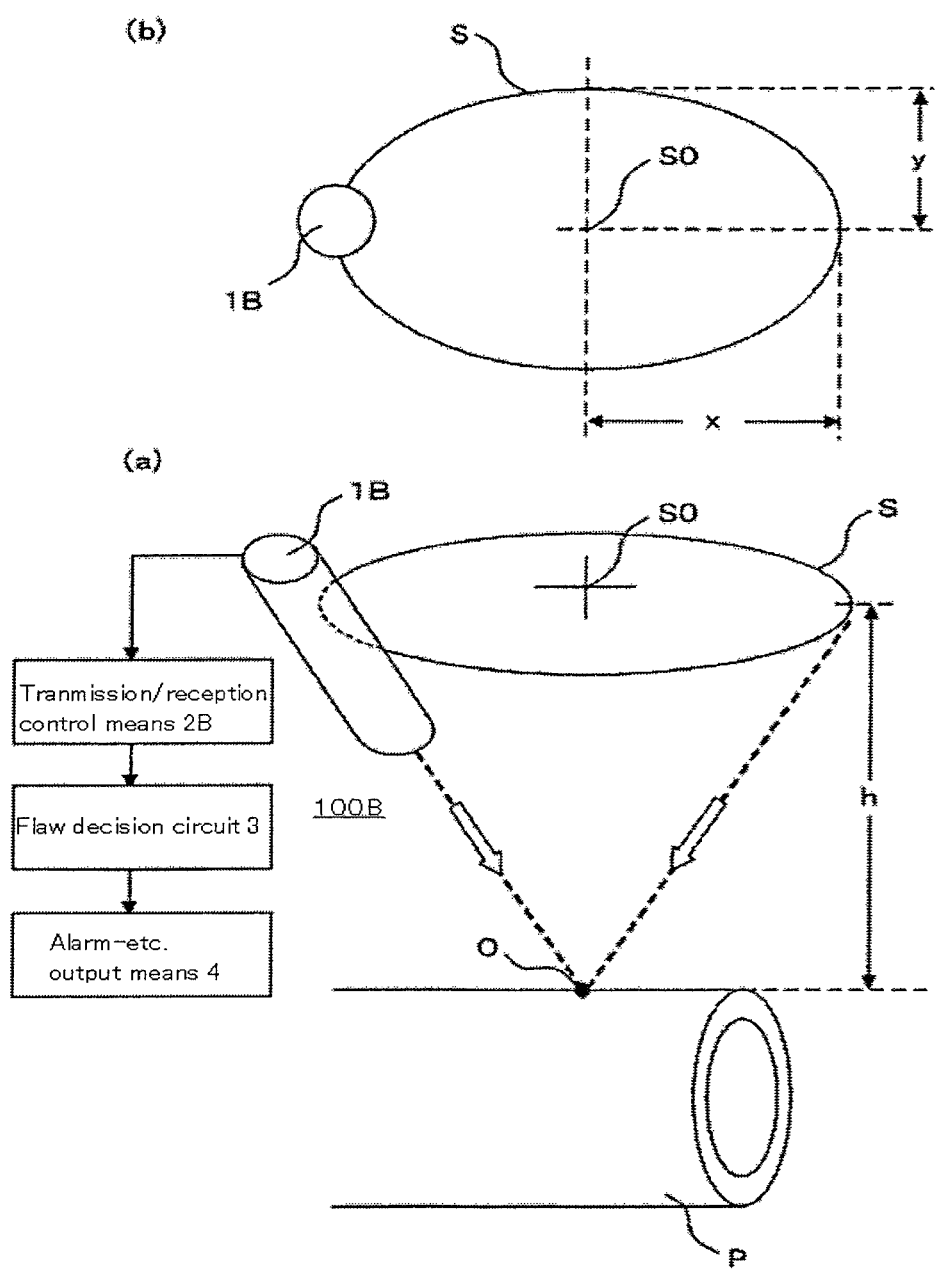
FIG. 6 is a schematic diagram showing an outlined configuration of an ultrasonic testing apparatus according to a fourth embodiment of the present invention.
Figure 7:
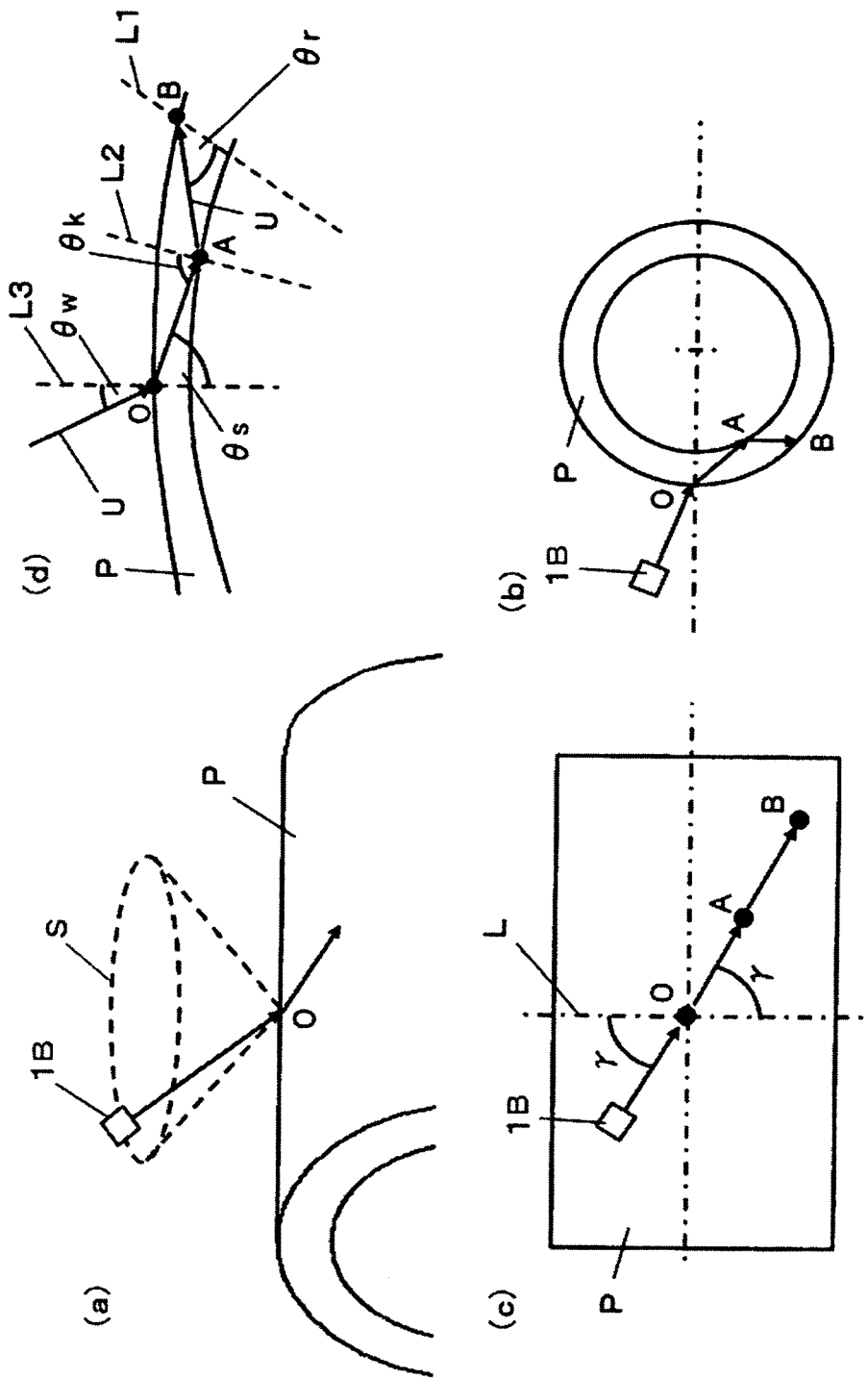
FIG. 7 is an explanatory schematic diagram showing propagation behaviors of an ultrasonic wave in the ultrasonic testing apparatus shown in FIG. 6.

FIG. 6 is a schematic diagram showing an outlined configuration of an ultrasonic testing apparatus according to the fourth embodiment of the present invention, of which FIG. 6A is a perspective view and FIG. 6B is a plan view. FIG. 7 is an explanatory schematic diagram showing propagation behaviors of ultrasonic waves in the ultrasonic testing apparatus shown in FIG. 6, of which FIG. 7A is a perspective view, FIG. 7B is a pipe-circumferential cross-sectional view, FIG. 7C is a plan view, and FIG. 7D is a cross-sectional view along a plane of propagation of ultrasonic waves (plane including points O, A, and B shown in FIG. 7B). As shown in FIG. 6, an ultrasonic testing apparatus 100B according to the present embodiment comprises an ultrasonic probe 1B and transmission/reception control means 2B for controlling transmission and reception of ultrasonic waves by the ultrasonic probe 1B. The ultrasonic testing apparatus 100B according to the present embodiment further comprises a flaw decision circuit 3 for detecting a flaw present in a pipe P by comparing an amplitude of a reflected echo from the pipe P to a predetermined threshold value, and alarm-etc. output means 4 for outputting a predetermined alarm etc. if a flaw is detected by the flaw decision circuit 3.

The ultrasonic probe 1B is arranged so as to face an external surface of the pipe P via a coupling medium (water in the present embodiment). More specifically, the ultrasonic probe 1B has such a configuration that its major diameter direction (x-direction in FIG. 6B) goes along an axial direction of the pipe P, its minor diameter direction (y-direction in FIG. 6B) goes along a circumference direction of the pipe P, and its center S0 can circle along an ellipsoid S that faces an axial center of the pipe P in order to hold a point of incidence O of a transmitted ultrasonic wave upon the pipe P to a specific position. It is to be noted that a mechanism, not shown, to permit the ultrasonic probe 1B to circle along the ellipsoid S can be manufactured as a comparatively simple structure by using well-known mechanical elements and, therefore, its detailed description is not included here.

The transmission/reception control means 2B according to the present embodiment comprises a pulser connected to transducers in the ultrasonic probe 1B to supply a pulse signal so as to have the transducers transmit an ultrasonic wave, and a receiver connected to the transducers to amplify a reflected echo received by this transducer.

According to the ultrasonic testing apparatus 100B having the above configuration, a flaw in the pipe P is detected by fixing the ultrasonic probe 1B to a predetermined position on a circular trajectory along the ellipsoid S so that a direction in which the flaw to be detected extends may be substantially orthogonal to a propagation direction of an ultrasonic wave transmitted from the ultrasonic probe 1B. Accordingly, flaws having a specific tilt can be detected. It is to be noted that the present embodiment has realized ultrasonic testing over a total length of the pipe P by spirally feeding the pipe P axially.

As in the cases of the first through third embodiments, the ultrasonic testing apparatus 100B according to the present embodiment features that an angle of incidence θw and a propagation angle γ are set based on a ratio of thickness to outer diameter t/D of the pipe P so that an internal refraction angle θk given in the above Equation (1) may be not less than 35° and not more than 60°, both inclusive. Reasons for this are described below more specifically with reference to FIG. 7 appropriately.

As shown in FIG. 7, ultrasonic waves transmitted from the ultrasonic probe 1B are supposed to enter the pipe P at point O on its external surface, reflected at point A on an internal surface of the pipe P, and reach point B on the external surface of the pipe P. Further, it is supposed that an angle (propagation angle) formed by a propagation direction of the ultrasonic wave that has entered through point O (propagation direction as viewed from a direction of a normal of a tangential plane of the pipe P including the point of incidence O) and a circumferential tangent L of the pipe P passing through the point of incidence O is to be γ (hereinafter also referred to as "propagation direction γ" appropriately), an external refraction angle at point B (angle formed by a normal L1 at point B on the pipe P and the ultrasonic wave beam U on an ultrasonic wave propagation plane shown in FIG. 7D) is θr, and an internal refraction angle at point A (angle formed by a normal L2 at point A on the pipe P and the ultrasonic wave beam U on the ultrasonic wave propagation plane shown in FIG. 7D) is θk. Further, it is supposed that an angle of incidence of an ultrasonic wave upon the pipe P (angle formed by a normal L3 at the point of incidence O on the pipe P and a pre-incidence ultrasonic wave beam U on an ultrasonic wave propagation plane shown in FIG. 7D) is θw and an angle of refraction of the ultrasonic wave upon the pipe P (angle formed by the normal L3 at the point of incidence O on the pipe P and the post-incidence ultrasonic wave beam U on the ultrasonic wave propagation plane shown in FIG. 7D) is θs.

The ultrasonic waves made incident upon the pipe P at the angle of incidence θw have geometric-optical propagation behaviors. That is, the ultrasonic waves made incident upon the pipe P at the angle of incidence θw propagate through the pipe P at an angle of refraction θs determined by the Snell's law. Then, as can be derived geometrically, the external refraction angle θr becomes equal to the angle of refraction θs. That is, the following Equation (7) is established:

[Eq. 10]

$$\sin\theta r = Vs/Vi \cdot \sin\theta w \quad (7)$$

In the above Equation (7), it is to be noted that Vs refers to a propagation speed of an ultrasonic wave propagating through the pipe P and Vi refers to a propagation speed of the ultrasonic wave in a coupling medium that fills a gap between the ultrasonic probe 1B and the pipe P.

Further, as can be derived from the above-described Equations (7) and (4) through (6), internal refraction angle θk given in the above Equation (1) is a function of the angle of incidence θw, the propagation angle γ, and a ratio of thickness to outer diameter t/D of the pipe P. Further, it is minimized to be equal to the external refraction angle θr (=angle of refraction θs) when the propagation direction γ of the ultrasonic wave agrees with an axial direction of the pipe P (that is, propagation angle γ=90°) and maximized when the propagation direction γ of the ultrasonic wave agrees with a circumference direction of the pipe P (that is, propagation angle γ=0°), thus being given by the following Equation (8):

[Eq. 11]

$$\theta k = \sin^{-1}\left(\frac{\sin\theta r}{1 - 2(t/D)}\right) \quad (8)$$

In this case, if the ratio of thickness to outer diameter t/D of the pipe P is about several percent, a difference between the internal refraction angle θk and the external refraction angle θr calculated by the above Equation (8) is limited to about 10° or less. Therefore, a difference between an internal refraction angle θk in the case of detecting an internal surface flaw extending in the axial direction of the pipe P (to be detected by an ultrasonic wave whose propagation direction γ agrees with the circumference direction of the pipe P) and an internal refraction angle θk in the case of detecting an internal surface flaw extending in the circumference direction of the pipe P (to be detected by an ultrasonic wave whose propagation direction γ agrees with the axial direction of the pipe P) is limited to about 10° or less, thus eliminating significant differences in detectability of both of the internal surface flaws. However, if t/D of the pipe P becomes 15% or more, the internal refraction angle θk calculated by the above Equation (8) becomes larger than the external refraction angle θr by as much as 20° (that is, the internal refraction angle θk increases by as much as 20° by turning the propagation direction γ from the axial direction to the circumference direction of the pipe P), thereby greatly deteriorating the detectability for the internal surface flaws extending in the axial direction of the pipe P. Similarly, the detectability for the internal surface flaws having a tilt angle between the axial direction and the circumference direction of the pipe P also deteriorates as the internal refraction angle θk increases.

To suppress a deterioration in detectability for internal surface flaws that is caused by a variation in internal refraction angle θk described above, they can be detected with such an internal refraction angle θk as to substantially equalize reflected echo intensities at the internal surface flaws irrespective of the tilt angles of the internal surface flaws (irrespective of the ultrasonic wave propagation direction γ). Such a range of the internal refraction angle θk is not less than 35° and not more than 60° as shown in FIG. 4 (preferably, not less than 35° and not more than 55° to suppress a change in echo intensity). Therefore, in the ultrasonic testing apparatus 100B according to the present embodiment, the angle of incidence θw and the propagation angle γ are set based on the ratio of thickness to outer diameter t/D of the pipe P so that the internal refraction angle θk may be not less than 35° and not more than 60°, both inclusive (preferably not less than 35° and not more than 55°, both inclusive, to suppress a change in echo intensity). More specifically, the propagation angle γ is set by circling the ultrasonic probe 1B along the ellipsoid S so that a direction in which a flaw to be detected extends may be substantially orthogonal to a propagation direction of an ultrasonic wave which is transmitted from the ultrasonic probe 1B. Further, by setting a shape of the ellipsoid S (major diameter, minor diameter, and distance between the point of incidence O of the ultrasonic wave and the ellipsoid S), the angle of incidence θw is set. It is thus possible to substantially equalize reflected echo intensities at internal surface flaws and hence detect the internal surface flaws with almost the same detectability irrespective of the ratio of thickness to outer diameter t/D and the tilt angles of the internal surface flaws of the pipe P.

Further, if a configuration for changing an amplitude of the receiver 221 based on a change in internal refraction angle θk in a range between 35° and 60°, both inclusive, is employed, it is preferable in that reflected echo intensities at the internal surface flaws can be equalized even more and hence detectabilities of the internal surface flaws can be equalized even more.

The following will describe a method for determining a shape of the ellipsoid S (major diameter, minor diameter, and distance between the point of incidence O of the ultrasonic wave and the ellipsoid S). As shown in FIG. 6, if it is supposed that the major diameter of the ellipsoid S is 2x, its minor diameter is 2y, and the distance between the point of incidence O of the ultrasonic wave and the ellipsoid S is h, an angle of incidence θw (referred to as θw1) of an ultrasonic wave which is transmitted when the ultrasonic probe 1B is placed at the major diameter of the ellipsoid S and an angle of incidence θw (referred to as θw2) of the ultrasonic wave which is transmitted when the ultrasonic probe 1B is placed at the minor diameter of the ellipsoid S are given by the following Equations (9) and (10) respectively:

[Eq. 12]

$$\theta w1 = \tan^{-1}(x/h) \quad (9)$$

$$\theta w2 = \tan^{-1}(y/h) \quad (10)$$

With this, the shape of the ellipsoid S (x, y, h) is determined based on t/D of the pipe P subject to flaw detection so that the angles of incidence $\theta w1$ and $\theta w2$ given by the above Equations (9) and (10) may satisfy the following Equation (11) and that internal refraction angle $\theta k$ calculated from the angles of incidence $\theta w1$ and $\theta w2$ respectively may fall in a range between 35° and 60°, both inclusive.

[Eq. 13]

$$\sin \theta w2 = \sin \theta w1 \cdot \{1 - 2(t/D)\} \quad (11)$$

In the present embodiment, the ratio of thickness to outer diameter t/D of the pipe P has been equal to 11% and the shape of the ellipsoid S (x, y, and h) has been determined so that the angle of incidence $\theta w1$ given by the above Equation (9) may be about 18° and the angle of incidence $\theta w2$ given by the above Equation (10) may be about 14°. Such angles of incidence $\theta w1$ and $\theta w2$ can satisfy the above Equation (11) and cause the internal refraction angle $\theta k$ given by the above Equation (1) to fall in a range between 35° and 60°, both inclusive.

Table 4 shows results of calculations of the propagation angle $\gamma$, the angle of incidence $\theta w$, the external refraction angle $\theta r$, and the internal refraction angle $\theta k$ of the ultrasonic wave in a case where the ultrasonic probe 1B in the ultrasonic testing apparatus 100B was circled along the ellipsoid S whose shape was determined as described above. In these calculations, Equations (1) and (4) through (7) described above were used. Further, in Equation (7), Vs=3200 m/sec (propagation speed of an ultrasonic shear wave through the steel pipe) and Vi=1500 m/sec (propagation speed of ultrasonic longitudinal waves in water).

TABLE 4

| propagation angle $\gamma$(°) | angle of incidence $\theta w$(°) | external refraction angle $\theta r$(°) | internal refraction angle $\theta k$(°) |
|---|---|---|---|
| 90 | 18 | 42 | 42 |
| 60 | 17 | 38 | 41 |
| 30 | 15 | 33 | 42 |
| 0 | 14 | 31 | 42 |

As shown in Table 4, it is possible not only to keep, at a tilt angle of an internal surface flaw in a range between 0° and 90°, both inclusive, (hence range of the propagation angle $\gamma$ of the ultrasonic wave between 0° and 90°, both inclusive), an internal refraction angle $\theta k$ in a range between 35° and 60°, both inclusive, but also to keep it to almost a constant value. Although Table 4 shows only the case of propagation angle $\gamma$ of the ultrasonic wave being in a range between 0° and 90°, it is actually possible to keep the internal refraction angle $\theta k$ to almost a constant value in condition where the propagation angle $\gamma$ is in a range between 0° and 360°. It is thus possible to substantially equalize detectabilities for internal surface flaws having any tilt angles in the range between 0° and 360°.

The invention claimed is:

1. A method for performing ultrasonic testing comprising the steps of:
    arranging an ultrasonic probe which comes in an ultrasonic phased array probe in which a plurality of transducers are arrayed so as to face an external surface of a tubular test object;
    setting a circumferential angle of incidence $\alpha i$ of an ultrasonic wave to be transmitted from said ultrasonic probe upon said tubular test object and an axial angle of incidence $\beta i$ of the ultrasonic wave to be transmitted from said ultrasonic probe upon said tubular test object based on a ratio of thickness to outer diameter t/D of said tubular test object so that an internal refraction angle $\theta k$ calculated from said circumferential angle of incidence $\alpha i$, said axial angle of incidence $\beta i$, and said ratio of thickness to outer diameter t/D of the tubular test object may be not less than 35° and not more than 60°;
    transmitting an ultrasonic wave to said tubular test object from said ultrasonic probe in which said circumferential angle of incidence $\alpha i$ and said axial angle of incidence $\beta i$ are set;
    receiving an ultrasonic wave reflected from said tubular test object by said ultrasonic probe; and
    processing the received ultrasonic wave to detect a flaw on said tubular test object,
    wherein in the step of setting said circumferential angle of incidence $\alpha i$ and said axial angle of incidence $\beta i$, by electrically controlling transmission time-shift or reception time-shift of an ultrasonic wave by said plurality of transducers, at least one of said circumferential angle of incidence $\alpha i$ and said axial angle of incidence $\beta i$ of the ultrasonic wave transmitted to said tubular test object is electrically adjusted.

2. A method for manufacturing a seamless pipe or tube, comprising:
    a first step of piercing a billet to manufacture a seamless pipe or tube; and
    a second step of detecting a flaw in the seamless pipe or tube manufactured by said first step, by using the ultrasonic testing method according to claim 1.

3. The ultrasonic testing method according to claim 1, wherein
    in the step of setting said circumferential angle of incidence $\alpha i$ and said axial angle of incidence $\beta i$, said circumferential angle of incidence $\alpha i$ and said axial angle of incidence $\beta i$ are set so that a propagation direction of an ultrasonic wave made incident upon said tubular test object calculated from said circumferential angle of incidence $\alpha i$ and said axial angle of incidence $\beta i$ may be substantially orthogonal to an extension direction of a flaw to be detected, and then at least one of said circumferential angle of incidence $\alpha i$ and said axial angle of incidence $\beta i$ is electrically adjusted so that said internal refraction angle $\theta k$ may be not less than 35° and not more than 60°.

4. A method for performing ultrasonic testing comprising the steps of:
    arranging an ultrasonic probe so as to face an external surface of a tubular test object;
    setting a circumferential angle of incidence $\alpha i$ of an ultrasonic wave to be transmitted from said ultrasonic probe upon said tubular test object and an axial angle of incidence $\beta i$ of the ultrasonic wave to be transmitted from said ultrasonic probe upon said tubular test object based on a ratio of thickness to outer diameter t/D of said tubular test object so that an internal refraction angle $\theta k$ calculated from said circumferential angle of incidence αi, said axial angle of incidence βi, and said ratio of thickness to outer diameter t/D of the tubular test object may be not less than 35° and not more than 60°;

transmitting an ultrasonic wave to said tubular test object from said ultrasonic probe in which said circumferential angle of incidence αi and said axial angle of incidence βi are set;

receiving an ultrasonic wave reflected from said tubular test object by said ultrasonic probe; and processing the received ultrasonic wave to detect a flaw on said tubular test object, wherein in the step of setting said circumferential angle of incidence αi and said axial angle of incidence βi, positioning said ultrasonic probe so as to obtain said circumferential angle of incidence αi and said axial angle of incidence βi for which said internal refraction angle θk calculated by the following Equation (1) may be not less than 35° and not more than 60°:

$$\theta k = \cos^{-1}(\cos \theta r \cdot \cos \phi - \sin \theta r \cdot \cos \gamma \cdot \sin \phi) \qquad (1)$$

where a propagation angle γ, an external angle θr, and an angle φ are given by the following equations (2) through (4) respectively:

$$\gamma = \tan^{-1}\left(\frac{\sin \beta i}{\cos \beta i \cdot \sin \alpha i}\right) \qquad (2)$$

$$\theta r = \sin^{-1}\left([(Vs/Vi)^2 \cdot (\sin^2 \beta i + \cos^2 \beta i - \sin^2 \alpha i)]^{1/2}\right) \qquad (3)$$

$$\phi = \sin^{-1}(k \cdot \sin \theta') - \theta' \qquad (4)$$

where, in the above Equation (3), Vs refers to a propagation speed of an ultrasonic wave propagating through the tubular test object and Vi refers to a propagation speed of the ultrasonic wave in a coupling medium that fills a gap between the ultrasonic probe and the tubular test object, k and θ' in the above equation (4) are given by the following Equations (5) and (6) respectively:

$$k = \frac{1}{1 - 2(t/D)} \qquad (5)$$

$$\tan \theta' = \cos \gamma \cdot \tan \theta r. \qquad (6)$$

5. The ultrasonic testing method according to claim 4, wherein in the step of setting said circumferential angle of incidence αi and said axial angle of incidence βi, said circumferential angle of incidence αi and said axial angle of incidence βi are set so that a propagation direction of an ultrasonic wave made incident upon said tubular test object calculated from said circumferential angle of incidence αi and said axial angle of incidence βi may be substantially orthogonal to an extension direction of a flaw to be detected, and then at least one of said circumferential angle of incidence αi and said axial angle of incidence βi is adjusted so that said internal refraction angle θk may be not less than 35° and not more than 60°.

6. A method for manufacturing a seamless pipe or tube, comprising:
a first step of piercing a billet to manufacture a seamless pipe or tube; and
a second step of detecting a flaw in the seamless pipe or tube manufactured by said first step, by using the ultrasonic testing method according to claim 4.

7. A method for performing ultrasonic testing comprising the steps of:
arranging an ultrasonic probe so as to face an external surface of a tubular test object;
setting an angle of incidence θw of an ultrasonic wave to be transmitted from said ultrasonic probe upon said tubular test object and a propagation angle γ of the ultrasonic wave to be made incident upon said tubular test object based on a ratio of thickness to outer diameter t/D of said tubular test object so that an internal refraction angle θk calculated from said angle of incidence θw, said propagation angle γ, and the ratio of thickness to outer diameter t/D of said tubular test object may be not less than 35° and not more than 60°;
transmitting an ultrasonic wave to said tubular test object from said ultrasonic probe in which said angle of incidence θw and propagation angle γ are set;
receiving an ultrasonic wave reflected from said tubular test object by said ultrasonic probe; and
processing the received ultrasonic wave to detect a flaw on said tubular test object,
wherein the step of setting said angle of incidence θw and said propagation angle γ, positioning said ultrasonic probe so as to obtain said angle of incidence θw and propagation angle γ for which said internal refraction angle θk is calculated by the following Equation (1) may be not less than 35° and not more than 60°:

$$\theta k = \cos^{-1}(\cos \theta r \cdot \cos \phi - \sin \theta r \cdot \cos \gamma \cdot \sin \phi) \qquad (1)$$

where an external refraction angle θr and an angle φ in the above Equation (1) are given by the following Equations (7) and (4) respectively:

$$\sin \theta r = Vs/Vi \cdot \sin \theta w \qquad (7)$$

$$\phi = \sin^{-1}(k \cdot \sin \theta') - \theta' \qquad (4)$$

where, in the above Equation (7), Vs refers to a propagation speed of an ultrasonic wave propagating through the tubular test object and Vi refers to a propagation speed of the ultrasonic wave in coupling medium that fills gap between the ultrasonic probe and the tubular test object, and k and θ' in the above Equation (4) are given by the following Equations (5) and (6) respectively $$k = \frac{1}{1 - 2(t/D)} \qquad (5)$$

$$\tan \theta' = \cos \gamma \cdot \tan \theta r. \qquad (6)$$

8. A method for manufacturing a seamless pipe or tube, comprising:
a first step of piercing a billet to manufacture a seamless pipe or tube; and
a second step of detecting a flaw in the seamless pipe or tube manufactured by said first step, by using the ultrasonic testing method according to claim 7.

9. The ultrasonic testing method according to claim 7, wherein
   in the step of setting said angle of incidence θw and said propagation angle γ, said propagation angle γ is set so that a propagation direction of an ultrasonic wave made incident upon said tubular test object may be substantially orthogonal to an extension direction of a flaw to be detected, and then said angle of incidence θw is adjusted so that said internal refraction angle θk may be not less than 35° and not more than 60°.

* * * * *

UNITED STATES PATENT AND TRADEMARK OFFICE
CERTIFICATE OF CORRECTION

PATENT NO. : 8,495,915 B2
APPLICATION NO. : 11/990934
DATED : July 30, 2013
INVENTOR(S) : Masaki Yamano Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1464 days.

Signed and Sealed this
Fifteenth Day of September, 2015

Michelle K. Lee
*Director of the United States Patent and Trademark Office*